(12) United States Patent
Matthews et al.

(10) Patent No.: US 7,390,645 B2
(45) Date of Patent: Jun. 24, 2008

(54) LACTOSE REPRESSOR PROTEINS WITH INCREASED OPERATOR DNA BINDING AFFINITY

(75) Inventors: Kathleen S. Matthews, Houston, TX (US); Catherine M. Foster, Houston, TX (US); Liskin Swint-Kruse, Pearland, TX (US)

(73) Assignee: William Marsh Rice University, Houston, TX (US)

( * ) Notice: Subject to any disclaimer, the term of this patent is extended or adjusted under 35 U.S.C. 154(b) by 770 days.

(21) Appl. No.: 10/197,053

(22) Filed: Jul. 17, 2002

(65) Prior Publication Data

US 2002/0193568 A1 Dec. 19, 2002

Related U.S. Application Data

(63) Continuation-in-part of application No. 09/736,836, filed on Dec. 14, 2000, now abandoned, and a continuation-in-part of application No. 09/554,537, filed as application No. PCT/US98/24949 on Nov. 20, 1998, now abandoned.

(60) Provisional application No. 60/066,213, filed on Nov. 20, 1997, provisional application No. 60/172,464, filed on Dec. 17, 1999.

(51) Int. Cl.
  *C12N 1/21* (2006.01)
  *C07K 14/245* (2006.01)
(52) U.S. Cl. .................. 435/252.33; 435/252.3; 530/350
(58) Field of Classification Search .......... 530/350; 435/243, 252.1, 252.3
See application file for complete search history.

(56) References Cited

FOREIGN PATENT DOCUMENTS

| AT | 397 812 | 7/1994 |
|---|---|---|
| EP | 0 685 560 | 12/1995 |
| IE | 71198 | 2/1997 |
| WO | WO 97 04110 | 2/1997 |
| WO | WO 97 49813 | 12/1997 |

OTHER PUBLICATIONS

Suckow et al. J. Mol. Biol. 261: 509-523, 1996.*
LeClerc, J.E. et al. Ultraviolet Light Induces Different Spectra of lacI Sequence Changes in Vegetative and Conjugating Cells of *Escherichia coli* J. Mol. Biol. 203:619-633 1988.*
Chang, W.-I and Matthews, K.S., "Role of Asp$^{274}$ in *lac* Repressor: diminished sugar binding and altered conformational effects in mutants," *Biochemistry* 34:9227-9234 (1995).
Falcon, C.M. et al., "Designed disulfide between N-terminal domains of lactose repressor disrupts allosteric linkage" *J. Biol. Chem.* (1997) 272: 26818-26821.
Falcon, C.M. and Matthews, K.S., "Interference of lactose repressor hinge region function with the introduction of glycine sequences" poster presented at The Protein Society's 12$^{th}$ Symposium (San Diego, CA Jul. 25-29, 1998) (poster session abstract).
Falcon, C.M. and Matthews, K.S., "Alteration of lactose repressor function upon mutation within the hinge region" presentation at the 12$^{th}$ Annual Gibbs Conference on Biothermodynamics (Carbondale, Illinois Oct. 3-6, 1998) (presentation abstract).
Falcon, C.M. and Matthews, K.S., "Operator DNA sequence variation enhances high affinity binding by hinge helix mutants of lactose repressor protein" *Biochemistry* 39:11074-83 (2000).
Falcon, C.M. et al,. "Glycine insertion in the hinge region of lactose repressor protein alters DNA binding" *J. Biol. Chem.* (1999) 274: 30849-30857.
Falcon, C.M., "Chapter 3: Glycine Insertions," In *Role of lac repressor hinge region and operator DNA sequence in complex formation*. Rice University Ph.D. thesis (Houston, Texas; Apr. 1999) pp. 46-82.
Fieck et al, "Modifications of The *E. coli* Lac Repressor for Expression In Eukaryotic Cells: Effects of Nuclear Signal Sequences on Protein Activity and Nuclear Acumulation", *Nucleic Acids Research* 20: 1785-1791 (1992).
Jahreis, K. and Lengeler, J.W., "Molecular analysis of ScR repressors and of a ScR-FruR hybrid repressor for sucrose and D-fructose specific regulons from enteric bacteria," *Molecular Microbiology* 9(1):195-209 (1993).
Kalodimos, C.G.; Folkers, G.E.; Boelens, R.; Kapten, R. *Proc. Natl. Acad. Sci. U. S. A.* 98:6039-6044 (2001).
Kolkhof, P., "Specificities of three tight-binding Lac repressors" *Nucl. Acids Res* 20:5035-5039 (1992).
Kolkhof, P., Teichmann, D., Kisters-Woike, B., von Wilcken-Bergmann, B., and Muller-Hill, B., Lac repressor with the helix-turn-helix motif of lambda cro binds to lac operator. *EMBO J.* 11:3031-38 (1992).
Lewis, M. et al., "Crystal Structure of the Lactose Operon Repressor and Its Complexes with DNA and Inducer", *Science* 271: 1247-1254 (1996).
Matthews, K.S.; Nichols, J.C., "Lactose Repressor Protein: Functional Properties and Structure. *Prog.*", *Nucl. Acid Res. Mol. Biol.* 58: 127-163 (1998).

(Continued)

*Primary Examiner*—Nancy Vogel
(74) *Attorney, Agent, or Firm*—Howrey LLP (57) ABSTRACT

The present invention provides altered lac repressor proteins that recognize the lactose operator with increased affinity and have either normal or enhanced ligand responsivity. For example, the lac repressor Gln60Gly mutant protein exhibits increased binding affinity for lactose operator DNA, while maintaining near-normal responsivity to IPTG. Alternatively, the present invention provides modified repressors which exhibit responsiveness to an alternative ligand, such as arabinose, or have enhanced responsivity to IPTG. For example, Gln60Gly/Leu148Phe binds with wild-type affinity to lactose operator DNA and exhibits enhanced responsivity to IPTG. The present invention also provides for repressors that exhibit both characteristics: increased affinity for lactose operator and enhanced ligand responsivity. Enhanced ligand response enables induction of gene expression to be finely controlled by a researcher. DNA sequences encoding the altered lac repressor proteins and bacterial and eukaryotic cells containing altered lac repressor proteins are also provided.

8 Claims, 3 Drawing Sheets

OTHER PUBLICATIONS

Nichols, J.C. et al., "Model of Lactose Repressor Core Based on Alignment with Sugar-binding Proteins Is Concordant with Genetic and Chemical Data", *J. Biol. Chem.* 268: 17602-17612 (1993).

Sams, C. et al., "Predicted structure of the sugar-binding site of the *lac* repressor", *Nature* 310:429-430 (1984).

Weickert and Adhya, "A Family of Bacterial Regulators Homologous to Gal and Lac Repressors", *Journal of Biological Chemistry* 267:15869-15874 (1992).

Mirny, L.A. and Gelfand, M.S. "Using orthologous and paralogous proteins to identify specifity-determining residues in bacterial transcription factors," *J. Mol. Biol.*, 321:7-20 (2002).

Swint-Kruse et al. Gibbs Meeting Poster, Sep. 29, 2002.

* cited by examiner

SEQUENCE LISTING

<160> NUMBER OF SEQ ID NOS: 6

<210> SEQ ID NO 1
<211> LENGTH: 360
<212> TYPE: PRT
<213> ORGANISM: Escherichia coli

<400> SEQUENCE: 1

Met Lys Pro Val Thr Leu Tyr Asp Val Ala Glu Tyr Ala Gly Val Ser
1               5                   10                  15

Tyr Gln Thr Val Ser Arg Val Val Asn Gln Ala Ser His Val Ser Ala
            20                  25                  30

```
Lys Thr Arg Glu Lys Val Glu Ala Ala Met Ala Glu Leu Asn Tyr Ile
            35                  40                  45

Pro Asn Arg Val Ala Gln Gln Leu Ala Gly Lys Gln Ser Leu Leu Ile
    50                  55                  60

Gly Val Ala Thr Ser Ser Leu Ala Leu His Ala Pro Ser Gln Ile Val
65                  70                  75                  80

Ala Ala Ile Lys Ser Arg Ala Asp Gln Leu Gly Ala Ser Val Val Val
                85                  90                  95

Ser Met Val Glu Arg Ser Gly Val Glu Ala Cys Lys Ala Ala Val His
                100                 105                 110

Asn Leu Leu Ala Gln Arg Val Ser Gly Leu Ile Ile Asn Tyr Pro Leu
            115                 120                 125

Asp Asp Gln Asp Ala Ile Ala Val Glu Ala Ala Cys Thr Asn Val Pro
        130                 135                 140

Ala Leu Phe Leu Asp Val Ser Asp Gln Thr Pro Ile Asn Ser Ile Ile
145                 150                 155                 160

Phe Ser His Glu Asp Gly Thr Arg Leu Gly Val Glu His Leu Val Ala
                165                 170                 175

Leu Gly His Gln Gln Ile Ala Leu Leu Ala Gly Pro Leu Ser Ser Val
            180                 185                 190

Ser Ala Arg Leu Arg Leu Ala Gly Trp His Lys Tyr Leu Thr Arg Asn
        195                 200                 205

Gln Ile Gln Pro Ile Ala Glu Arg Gly Asp Trp Ser Ala Met Ser
    210                 215                 220

Gly Phe Gln Gln Thr Met Gln Met Leu Asn Glu Gly Ile Val Pro Thr
225                 230                 235                 240

Ala Met Leu Val Ala Asn Asp Gln Met Ala Leu Gly Ala Met Arg Ala
                245                 250                 255

Ile Thr Glu Ser Gly Leu Arg Val Gly Ala Asp Ile Ser Val Val Gly
            260                 265                 270

Tyr Asp Asp Thr Glu Asp Ser Ser Cys Tyr Ile Pro Pro Leu Thr Thr
        275                 280                 285

Ile Lys Gln Asp Phe Arg Leu Leu Gly Gln Thr Ser Val Asp Arg Leu
290                 295                 300

Leu Gln Leu Ser Gln Gly Gln Ala Val Lys Gly Asn Gln Leu Leu Pro
305                 310                 315                 320

Val Ser Leu Val Lys Arg Lys Thr Thr Leu Ala Pro Asn Thr Gln Thr
                325                 330                 335

Ala Ser Pro Arg Ala Leu Ala Asp Ser Leu Met Gln Leu Ala Arg Gln
            340                 345                 350

Val Ser Arg Leu Glu Ser Gly Gln
        355                 360

<210> SEQ ID NO 2
<211> LENGTH: 360
<212> TYPE: PRT
<213> ORGANISM: Escherichia coli

<400> SEQUENCE: 2

Met Lys Pro Val Thr Leu Tyr Asp Val Ala Glu Tyr Ala Gly Val Ser
1               5                   10                  15

Tyr Gln Thr Val Ser Arg Val Val Asn Gln Ala Ser His Val Ser Ala
            20                  25                  30

Lys Thr Arg Glu Lys Val Glu Ala Ala Met Ala Glu Leu Asn Tyr Ile
```

```
                  35                  40                  45
Pro Asn Arg Val Ala Gln Gln Leu Ala Gly Lys Gly Ser Leu Leu Ile
 50                  55                  60
Gly Val Ala Thr Ser Ser Leu Ala Leu His Ala Pro Ser Gln Ile Val
 65                  70                  75                  80
Ala Ala Ile Lys Ser Arg Ala Asp Gln Leu Gly Ala Ser Val Val Val
                 85                  90                  95
Ser Met Val Glu Arg Ser Gly Val Glu Ala Cys Lys Ala Ala Val His
                100                 105                 110
Asn Leu Leu Ala Gln Arg Val Ser Gly Leu Ile Ile Asn Tyr Pro Leu
                115                 120                 125
Asp Asp Gln Asp Ala Ile Ala Val Glu Ala Ala Cys Thr Asn Val Pro
130                 135                 140
Ala Leu Phe Leu Asp Val Ser Asp Gln Thr Pro Ile Asn Ser Ile Ile
145                 150                 155                 160
Phe Ser His Glu Asp Gly Thr Arg Leu Gly Val Glu His Leu Val Ala
                165                 170                 175
Leu Gly His Gln Gln Ile Ala Leu Leu Ala Gly Pro Leu Ser Ser Val
                180                 185                 190
Ser Ala Arg Leu Arg Leu Ala Gly Trp His Lys Tyr Leu Thr Arg Asn
                195                 200                 205
Gln Ile Gln Pro Ile Ala Glu Arg Glu Gly Asp Trp Ser Ala Met Ser
210                 215                 220
Gly Phe Gln Gln Thr Met Gln Met Leu Asn Glu Gly Ile Val Pro Thr
225                 230                 235                 240
Ala Met Leu Val Ala Asn Asp Gln Met Ala Leu Gly Ala Met Arg Ala
                245                 250                 255
Ile Thr Glu Ser Gly Leu Arg Val Gly Ala Asp Ile Ser Val Val Gly
                260                 265                 270
Tyr Asp Asp Thr Glu Asp Ser Ser Cys Tyr Ile Pro Pro Leu Thr Thr
                275                 280                 285
Ile Lys Gln Asp Phe Arg Leu Leu Gly Gln Thr Ser Val Asp Arg Leu
                290                 295                 300
Leu Gln Leu Ser Gln Gly Gln Ala Val Lys Gly Asn Gln Leu Leu Pro
305                 310                 315                 320
Val Ser Leu Val Lys Arg Lys Thr Thr Leu Ala Pro Asn Thr Gln Thr
                325                 330                 335
Ala Ser Pro Arg Ala Leu Ala Asp Ser Leu Met Gln Leu Ala Arg Gln
                340                 345                 350
Val Ser Arg Leu Glu Ser Gly Gln
                355                 360

<210> SEQ ID NO 3
<211> LENGTH: 1083
<212> TYPE: DNA
<213> ORGANISM: Escherichia coli

<400> SEQUENCE: 3
gtgaaaccag taacgttata cgatgtcgca gagtatgccg gtgtctctta tcagaccgtt      60
tcccgcgtgg tgaaccaggc cagccacgtt tctgcgaaaa cgcgggaaaa agtggaagcg     120
gcgatggcgg agctgaatta cattcccaac cgcgtggcac aacaactggc gggcaaaggc     180
tcgttgctga ttggcgttgc cacctccagt ctggccctgc acgcgccgtc gcaaattgtc     240
gcggcgatta atctcgcgc cgatcaactg ggtgccagcg tggtggtgtc gatggtagaa     300
```

```
cgaagcggcg tcgaagcctg taaagcggcg gtgcacaatc ttctcgcgca acgcgtcagt    360
gggctgatca ttaactatcc gctggatgac caggatgcca ttgctgtgga agctgcctgc    420
actaatgttc cggcgttatt tcttgatgtc tctgaccaga cacccatcaa cagtattatt    480
ttctcccatg aagacggtac gcgactgggc gtggagcatc tggtcgcatt gggtcaccag    540
caaatcgcgc tgttagcggg cccattaagt tctgtctcgg cgcgtctgcg tctggctggc    600
tggcataaat atctcactcg caatcaaatt cagccgatag cggaacggga aggcgactgg    660
agtgccatgt ccggttttca acaaaccatg caaatgctga atgagggcat cgttcccact    720
gcgatgctgg ttgccaacga tcagatggcg ctgggcgcaa tgcgcgccat taccgagtcc    780
gggctgcgcg ttggtgcgga tatctcggta gtgggatacg acgataccga agacagctca    840
tgttatatcc cgccgtcaac caccatcaaa caggattttc gcctgctggg caaaccagc     900 gtggaccgct gctgcaact ctctcagggc caggcggtga agggcaatca gctgttgccc      960
gtctcactgg tgaaaagaaa aaccaccctg gcgcccaata cgcaaaccgc ctctccccgc   1020
gcgttggccg attcattaat gcagctggca cgacaggttt cccgactgga aagcgggcag   1080
tga                                                                 1083
```

<210> SEQ ID NO 4
<211> LENGTH: 306
<212> TYPE: PRT
<213> ORGANISM: Escherichia coli

<400> SEQUENCE: 4

```
Glu Asn Leu Lys Leu Gly Phe Leu Val Lys Gln Pro Glu Pro Trp
1               5                   10                  15

Phe Gln Thr Glu Trp Lys Phe Ala Asp Lys Ala Gly Lys Asp Leu Gly
                20                  25                  30

Phe Glu Val Ile Lys Ile Ala Val Pro Asp Gly Glu Lys Thr Leu Asn
            35                  40                  45

Ala Ile Asp Ser Leu Ala Ala Ser Gly Ala Lys Gly Phe Val Ile Cys
        50                  55                  60

Thr Pro Asp Pro Lys Leu Gly Ser Ala Ile Val Ala Lys Ala Arg Gly
65                  70                  75                  80

Tyr Asp Met Lys Val Ile Ala Val Asp Asp Gln Phe Val Asn Ala Lys
                85                  90                  95

Gly Lys Pro Met Asp Thr Val Pro Leu Val Met Met Ala Ala Thr Lys
                100                 105                 110

Ile Gly Glu Arg Gln Gly Gln Glu Leu Tyr Lys Glu Met Gln Lys Arg
            115                 120                 125

Gly Trp Asp Val Lys Glu Ser Ala Val Met Ala Ile Thr Ala Asn Glu
        130                 135                 140

Leu Asp Thr Ala Arg Arg Arg Thr Thr Gly Ser Met Asp Ala Leu Lys
145                 150                 155                 160

Ala Ala Gly Phe Pro Glu Lys Gln Ile Tyr Gln Val Pro Thr Lys Ser
                165                 170                 175

Asn Asp Ile Pro Gly Ala Phe Asp Ala Ala Asn Ser Met Leu Val Gln
            180                 185                 190

His Pro Glu Val Lys His Trp Leu Ile Val Gly Met Asn Asp Ser Thr
        195                 200                 205

Val Leu Gly Gly Val Arg Ala Thr Glu Gly Gln Gly Phe Lys Ala Ala
    210                 215                 220
```

```
Asp Ile Ile Gly Ile Gly Ile Asn Gly Val Asp Ala Val Ser Glu Leu
225                 230                 235                 240

Ser Lys Ala Gln Ala Thr Gly Phe Tyr Gly Ser Leu Leu Pro Ser Pro
                245                 250                 255

Asp Val His Gly Tyr Lys Ser Ser Glu Met Leu Tyr Asn Trp Val Ala
            260                 265                 270

Lys Asp Val Glu Pro Pro Lys Phe Thr Glu Val Thr Asp Val Val Leu
        275                 280                 285

Ile Thr Arg Asp Asn Phe Lys Glu Glu Leu Glu Lys Lys Gly Leu Gly
    290                 295                 300

Gly Lys
305

<210> SEQ ID NO 5
<211> LENGTH: 296
<212> TYPE: PRT
<213> ORGANISM: Escherichia coli

<400> SEQUENCE: 5

Met Asn Met Lys Lys Leu Ala Thr Leu Val Ser Ala Val Ala Leu Ser
1               5                   10                  15

Ala Thr Val Ser Ala Asn Ala Met Ala Lys Asp Thr Ile Ala Leu Val
                20                  25                  30

Val Ser Thr Leu Asn Asn Pro Phe Phe Val Ser Leu Lys Asp Gly Ala
            35                  40                  45

Gln Lys Glu Ala Asp Lys Leu Gly Tyr Asn Leu Val Val Leu Asp Ser
    50                  55                  60

Gln Asn Asn Pro Ala Lys Glu Leu Ala Asn Val Gln Asp Leu Thr Val
65                  70                  75                  80

Arg Gly Thr Lys Ile Leu Leu Ile Asn Pro Thr Asp Ser Asp Ala Val
                85                  90                  95

Gly Asn Ala Val Lys Met Ala Asn Gln Ala Asn Ile Pro Val Ile Thr
            100                 105                 110

Leu Asp Arg Gln Ala Thr Lys Gly Glu Val Val Ser His Ile Ala Ser
        115                 120                 125

Asp Asn Val Leu Gly Gly Lys Ile Ala Gly Asp Tyr Ile Ala Lys Lys
    130                 135                 140

Ala Gly Glu Gly Ala Lys Val Ile Glu Leu Gln Gly Ile Ala Gly Thr
145                 150                 155                 160

Ser Ala Ala Arg Glu Arg Gly Glu Gly Phe Gln Gln Ala Val Ala Ala
                165                 170                 175

His Lys Phe Asn Val Leu Ala Ser Gln Pro Ala Asp Phe Asp Arg Ile
            180                 185                 190

Lys Gly Leu Asn Val Met Gln Asn Leu Leu Thr Ala His Pro Asp Val
        195                 200                 205

Gln Ala Val Phe Ala Gln Asn Asp Glu Met Ala Leu Gly Ala Leu Arg
    210                 215                 220

Ala Leu Gln Thr Ala Gly Lys Ser Asp Val Met Val Val Gly Phe Asp
225                 230                 235                 240

Gly Thr Pro Asp Gly Glu Lys Ala Val Asn Asp Gly Lys Leu Ala Ala
                245                 250                 255

Thr Ile Ala Gln Leu Pro Asp Gln Ile Gly Ala Lys Gly Val Glu Thr
            260                 265                 270

Ala Asp Lys Val Leu Lys Gly Glu Lys Val Gln Ala Lys Tyr Pro Val
        275                 280                 285
```

Asp Leu Lys Leu Val Val Lys Gln
    290                 295

<210> SEQ ID NO 6
<211> LENGTH: 332
<212> TYPE: PRT
<213> ORGANISM: Escherichia coli

<400> SEQUENCE: 6

Met Asn Lys Lys Val Leu Thr Leu Ser Ala Val Met Ala Ser Met Leu
1               5                   10                  15

Phe Gly Ala Ala Ala His Ala Ala Asp Thr Arg Ile Gly Val Thr Ile
            20                  25                  30

Tyr Lys Tyr Asp Asp Asn Phe Met Ser Val Val Arg Lys Ala Ile Glu
        35                  40                  45

Gln Asp Ala Lys Ala Ala Pro Asp Val Gln Leu Leu Met Asn Asp Ser
    50                  55                  60

Gln Asn Asp Gln Ser Lys Gln Asn Asp Gln Ile Asp Val Leu Leu Ala
65                  70                  75                  80

Lys Gly Val Lys Ala Leu Ala Ile Asn Leu Val Asp Pro Ala Ala Ala
                85                  90                  95

Gly Thr Val Ile Glu Lys Ala Arg Gly Gln Asn Val Pro Val Val Phe
            100                 105                 110

Phe Asn Lys Glu Pro Ser Arg Lys Ala Leu Asp Ser Tyr Asp Lys Ala
        115                 120                 125

Tyr Tyr Val Gly Thr Asp Ser Lys Glu Ser Gly Ile Ile Gln Gly Asp
    130                 135                 140

Leu Ile Ala Lys His Trp Ala Ala Asn Gln Gly Trp Asp Leu Asn Lys
145                 150                 155                 160

Asp Gly Gln Ile Gln Phe Val Leu Leu Lys Gly Glu Pro Gly His Pro
                165                 170                 175

Asp Ala Glu Ala Arg Thr Thr Tyr Val Ile Lys Glu Leu Asn Asp Lys
            180                 185                 190

Gly Ile Lys Thr Glu Gln Leu Gln Leu Asp Thr Ala Met Trp Asp Thr
        195                 200                 205

Ala Gln Ala Lys Asp Lys Met Asp Ala Trp Leu Ser Gly Pro Asn Ala
    210                 215                 220

Asn Lys Ile Glu Val Val Ile Ala Asn Asn Asp Ala Met Ala Met Gly
225                 230                 235                 240

Ala Val Glu Ala Leu Lys Ala His Asn Lys Ser Ser Ile Pro Val Phe
                245                 250                 255

Gly Val Asp Ala Leu Pro Glu Ala Leu Ala Leu Val Lys Ser Gly Ala
            260                 265                 270

Leu Ala Gly Thr Val Leu Asn Asp Ala Asn Asn Gln Ala Lys Ala Thr
        275                 280                 285

Phe Asp Leu Ala Lys Asn Leu Ala Asp Gly Lys Gly Ala Ala Asp Gly
    290                 295                 300

Thr Asn Trp Lys Ile Asp Asn Lys Val Val Arg Val Pro Tyr Val Gly
305                 310                 315                 320

Val Asp Lys Asp Asn Leu Ala Glu Phe Ser Lys Lys
                325                 330

LACTOSE REPRESSOR PROTEINS WITH INCREASED OPERATOR DNA BINDING AFFINITY

The application is a continuation-in-part of U.S. patent application Ser. No. 09/736,836, filed Dec. 14, 2000, abandoned, which claims the benefit of U.S. Provisional Application Ser. No. 60/172,464, filed Dec. 17, 1999; and of U.S. patent application Ser. No. 09/554,537, filed on May 12, 2000, abandoned, which is a §371 national stage conversion of International Application Serial No. PCT/US98/24949, filed Nov. 20, 1998, claiming the benefit of U.S. Provisional Application No. 60/066,213, filed Nov. 20, 1997. The entire contents of each of the foregoing applications is herein incorporated by reference.

The United States government may own rights in the present invention pursuant to grant number R01 GM22441 from the National Institutes of Health.

BACKGROUND OF THE INVENTION

1. Field of the Invention

The present invention relates to repressor proteins that: (i) recognize the lactose operator with increased affinity compared to wild type protein and exhibit normal inducibility; (ii) recognize the lactose operator with normal affinity while exhibiting enhanced inducibility (i.e., increased sensitivity to normal inducing sugars or responsiveness to alternative ligands); or (iii) alternatively, repressor proteins exhibiting increased affinity for the lactose operator DNA and enhanced inducibility.

2. Description of Related Art

The lac repressor protein is a genetic regulatory protein used widely to control the expression of cloned genes and is the prototype for negative control of transcription initiation in *E. coli* (Jacob & Monod, 1961). The lac repressor normally regulates expression of the lactose metabolic enzymes and couples cellular response with environmental availability of metabolites (Miller & Reznikoff, 1980). Multiple vector systems are commercially available that employ this repressor protein in cloning genes and overexpressing their protein products. These systems rely on the ability of the lac repressor to inhibit transcriptional initiation in the absence of an inducer.

Figure 1:
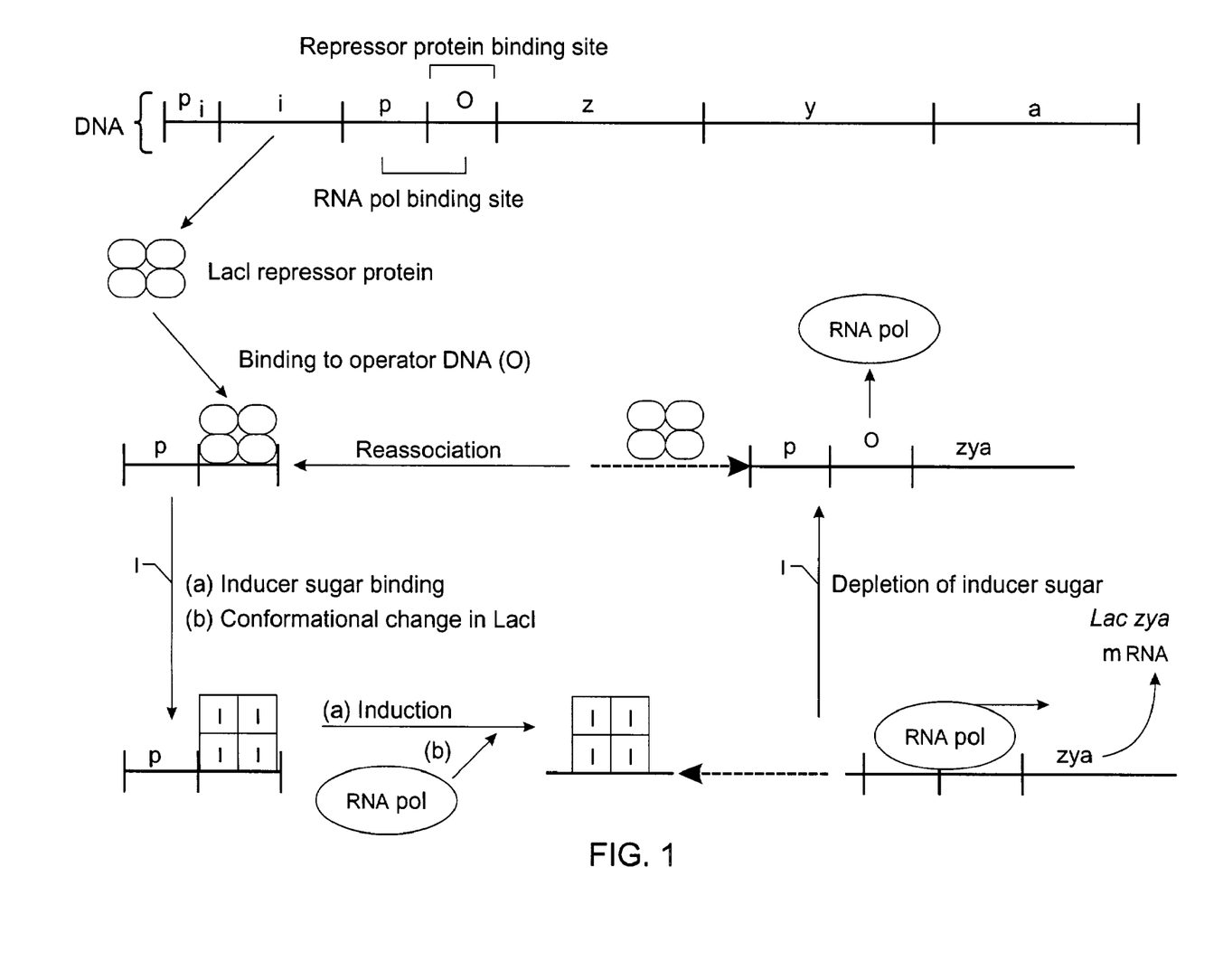
FIG. 1 is a schematic of lactose operon. The symbols correspond to the following: "$p_1$": promoter for "i" gene; "i": gene encoding lactose repressor protein (LacI); "p": promoter for lac enzymes; "O": lactose operator sequence (LacO); "z": gene encoding β-galactosidase; "y": gene encoding lac permease; "a": gene encoding thiogalactoside transacetylase; "I": inducer; "RNA pol": RNA polymerase.

FIG. 1 shows a schematic depicting how the lac repressor protein (LacI) and lac operator (LacO) work. The "i" gene product forms a tetrameric lactose repressor protein (LacI), which binds with high affinity to the partially two-fold symmetric lac operator DNA target sequence (LacO) that overlaps the promoter sequence "p". RNA polymerase binding, transcriptional initiation, and/or transcriptional elongation are inhibited when LacI occupies this site, thereby precluding production of the mRNA encoding the lac enzymes (z, y, a) (reviewed in Matthews & Nichols, 1998). In the absence of inducer sugars, the high affinity of LacI for LacO allows production of only small quantities of lacZYA mRNA. However, when inducer sugars, "I", are present, they bind LacI and cause a conformational change (depicted as (O→□)) (Lewis et al., 1996), which reduces the repressor's LacO binding affinity without having effect on its binding affinity for non-specific DNA (Lin & Riggs, 1975). Excess non-LacO DNA in the cell thereby effectively competes for binding to the protein and sequesters the repressor-inducer complex, allowing transcription of downstream lac mRNA to proceed for as long as inducer sugar is available. When inducer sugar levels are depleted, inducer dissociates from the repressor protein. The repressor protein subsequently reassumes the conformation with high affinity for LacO DNA, associates with LacO, and shuts down further synthesis of lac mRNA. The lactose regulatory cycle, therefore, involves association with both specific and non-specific DNA sequences, binding of inducer sugar molecules (ligands), and conformational shifts in response to these ligands.

When lactose is available in the environment, the low constitutive amounts of lac permease transport this sugar into the cell, and the correspondingly low levels of β-galactosidase result in production of the natural in vivo inducer, β-1,6-allolactose (Jobe & Bourgeois, 1972). When lactose levels are sufficiently decreased, the intracellular store of β-1,6-allolactose is depleted by β-galactosidase hydrolysis. These enzymatic activities ensure that the lac enzymes are not expressed except in the presence of lactose. In the *E. coli* genome, two additional operator sequences, located within the "i" and "z" genes, bind LacI with lower affinity (Miller & Reznikoff, 1980). Each dimer of the LacI tetramer binds one operator sequence; simultaneous binding of tetrameric LacI to two operators results in looped DNA and enhances repression (reviewed in Matthews & Nichols, 1998).

A different inducer, isopropyl-β,D-thiogalactoside (IPTG), that is not hydrolyzed by β-galactosidase, is commonly used to turn on transcription of genes cloned under control of the lac promoter-operator (in place of the z, y, and a genes depicted in FIG. 1). For expression systems that employ LacI/LacO interaction, the secondary operator sequences are usually not present, and the level of repression is consequently diminished.

For proteins that exert toxic effects or for which expression prior to addition of inducing sugar is otherwise deleterious, the ability to increase the efficacy of LacI repression while still maintaining a normal induction response would be very useful. Different, unique repressor proteins that recognize the primary lac operator sequence ($O^1$) with increased affinity, yet exhibit binding comparable to wild-type LacI in the presence of inducer (i.e., exhibit a normal induction response) would significantly enhance expression for many genes. Such repressor proteins could be used in any system in which the lac operator is used as the target sequence for transcriptional control and would provide an enhanced regulatory mechanism for the expression of cloned protein products.

SUMMARY OF THE INVENTION

The present invention provides an altered lac repressor protein comprising: (i) a lac repressor protein DNA binding domain that possesses increased binding affinity for LacO DNA sequence and a ligand binding domain of the natural lac repressor protein; or (ii) a lac repressor protein DNA binding domain with wild-type affinity for LacO DNA sequence and a ligand binding domain with enhanced responsivity to IPTG or other inducing ligands (i.e., more easily inducible); or (iii) a lac repressor protein DNA binding domain that possesses increased binding affinity for LacO DNA sequence and a ligand binding domain with enhanced responsivity to IPTG or other inducing ligands. The repressor protein of these embodiments of the invention comprises at least one amino acid change relative to the natural lac repressor protein.

The present invention also provides a method for preparing an altered lac repressor protein with increased affinity for lac operator DNA and normal responsivity to inducer ligand. The method of this embodiment comprises: a) altering at least one amino acid in the hinge region of a natural lac repressor protein by site-directed or random mutagenesis to produce altered lac repressor proteins; b) next, screening (using methods comprising, but not limited to, phenotypic evaluation and biophysical characterization) the altered lac repressor proteins to detect binding to lac operator DNA and normal responsivity to inducer ligands; and c) isolating those altered lac repressor proteins which exhibit increased affinity for lac operator DNA and normal responsivity to inducer ligands relative to the natural lac repressor protein.

Another embodiment of the present invention provides an additional method for preparing an altered lac repressor protein with increased affinity for lac operator DNA and normal responsivity to inducer ligand. The method of this embodiment comprises: a) altering at least one amino acid of a natural lac repressor proteins by random mutagenesis to produce altered lac repressor proteins; b) next, screening the altered lac repressor proteins to detect binding to /ac operator DNA and responsivity to inducer ligands; and c) isolating those altered lac repressor proteins which exhibit increased affinity for lac operator DNA and normal responsivity to inducer ligands relative to the natural lac repressor protein.

The present invention is also directed toward providing a method for preparing a repressor protein of the lac operator comprising: a) a LacI DNA binding domain that possesses normal binding affinity for LacO DNA sequence; and b) a ligand binding domain with enhanced responsivity to IPTG or an alternate inducer ligand (i.e., a ligand other than allolactose or IPTG). In this embodiment, the method comprises: a) altering at least one amino acid of LacI by random mutagenesis, (b) screening to detect responsivity to lower IPTG concentration or to alternate inducers, and c) isolating those altered repressors which exhibit comparable operator DNA binding affinity to wild-type lac repressor and enhanced responsivity to inducer ligands relative to the natural lac repressor.

Another aspect of this embodiment for the method of preparing lac repressor with normal DNA binding and alternate inducer responsivity comprises (a) fusion of the DNA binding domain of lac repressor to a ligand binding domain that is homologous to the lac repressor ligand binding domain (e.g., arabinose binding protein). The following step is (b) random or designed mutagenesis and screening to identify mutants with the ability to form oligomers and transmit the allosteric message. (Note that the homologous ligand binding proteins used in this embodiment are monomeric and do not transmit an allosteric message. Both dimerization and allostery are required for successful repressor function (Weickert and Adhya, 1992)). The third component is (c) isolating those altered repressors which exhibit normal DNA binding affinity for lac repressor and enhanced responsivity to inducer ligands relative to the natural lac repressor.

Another embodiment of the present invention provides a method for preparing an altered lac repressor protein comprising: fusion of a modified LacI DNA-binding domain that has increased affinity for LacO DNA sequence to the ligand binding domain of a lac repressor having enhanced responsivity to IPTG or to an alternate inducer.

Another embodiment of the present invention provides a method for preparing an altered lac repressor having increased affinity for DNA and enhanced responsivity to IPTG or to an alternate inducer: in this embodiment a DNA binding domain of a lac repressor, with at least one mutation that confers increased DNA binding affinity, is fused to a binding protein, having enhanced responsivity to IPTG or the ability to respond to another ligand and having the requisite mutations to bestow the ability to form oligomers and transmit an allosteric message between binding sites (see above).

The altered lac repressor proteins of the present invention, those having increased affinity for LacO DNA sequences, can be produced by site-specific mutation of the gene which encodes the LacI protein so as to produce the amino acid substitution of glycine for the glutamine as amino acid number 60. Glutamine is normally incorporated as amino acid number 60 of the LacI protein; this amino acid substitution is referred to in shorthand notation as Gln60Gly. Similarly, the LacI of the present invention, having an enhanced responsivity to inducer ligand can also be produced via other amino acid changes that result in increased affinity for lac operator and/or modified inducer responsivity. For example, those with enhanced inducer responsivity can be produced by substituting phenylalanine for the leucine found at position 148.

The present invention also provides DNA sequences encoding the altered lac repressor proteins and bacterial and eukaryotic cells containing the altered lac repressor proteins.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DESCRIPTION OF ILLUSTRATIVE EMBODIMENTS

Natural lac repressor protein is a homotetrameric protein of 150,000 Daltons with binding sites for four inducer molecules and two operator DNA sequences (Gilbert & Mueller-Hill, 1966; Riggs & Bourgeois, 1968; Butler et al., 1977; Whitson & Matthews, 1986). Within each subunit are two functional domains: a DNA-binding domain and an inducer binding domain (Lewis et al., 1996; Miller and Reznikoff, 1980). The DNA-binding domain has been identified with the N-terminal ~60 amino acids and alone exhibits specificity, but low affinity, for operator DNA (Ogata & Gilbert, 1978). The DNA-binding domain contains a helix-turn-helix (HTH) motif homologous to other DNA binding proteins (Brennan & Matthews, 1989). The inducer binding domain binds inducer and is involved in assembly of dimers and tetramers (Lewis et al., 1996; Friedman et al., 1995). The region that links these two domains is a short segment between amino acids ~50-60, termed the "hinge" or "hinge region" that forms a helical structure in the presence of operator DNA (Lewis et al., 1996). Formation of the hinge helix and its orientation on the lac operator DNA appear to be key to high affinity operator DNA binding for repressor proteins in this class (Lewis et al., 1996; Kalodimos et al., 2001).

Figure 2:
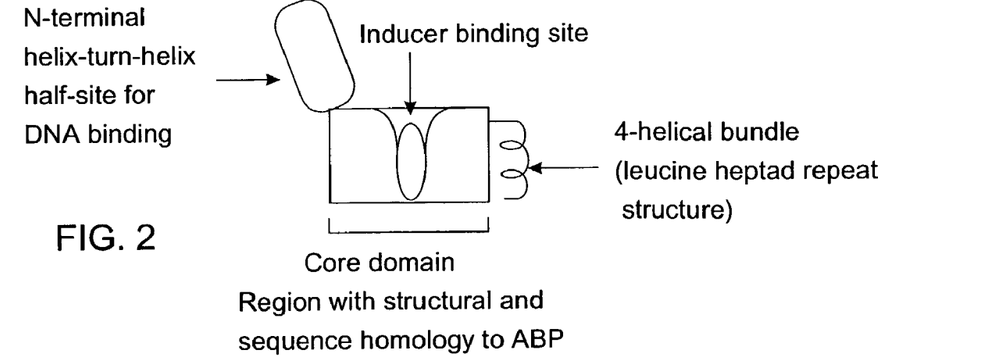
FIG. 2 is a schematic depiction of a monomer of lac repressor protein.
Figure 3:
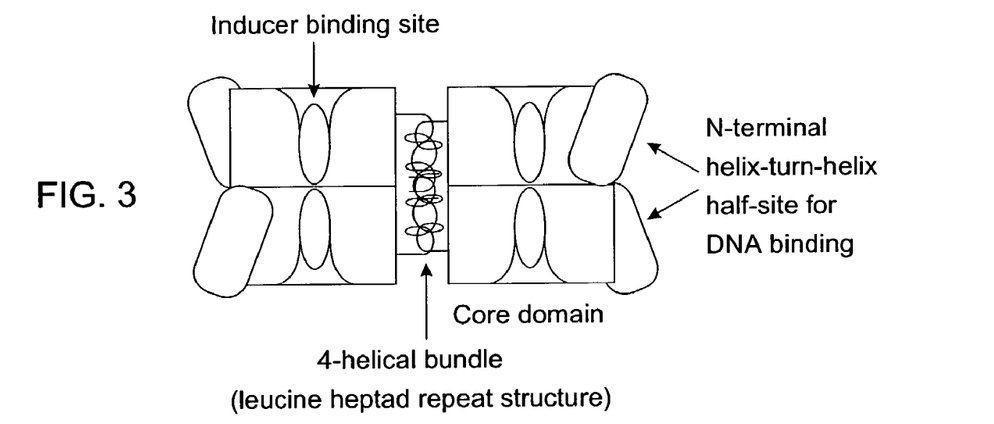
FIG. 3 is a schematic depiction of the tetrameric structure of lac repressor protein, laid open to view the dimer-dimer assembly.
Figure 4:
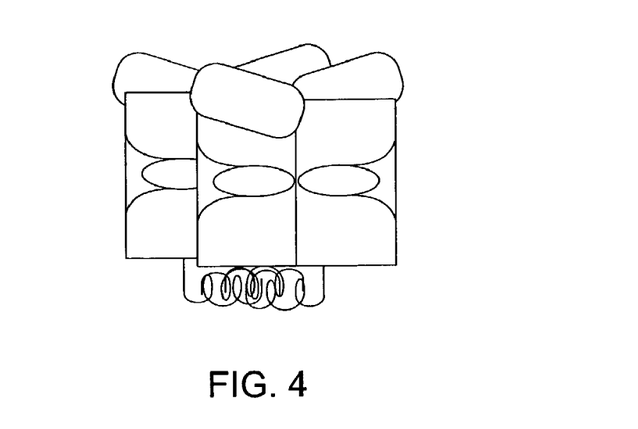
FIG. 4 is a schematic depiction of the tetrameric structure of lac repressor protein in its fully folded form.
Figure 5:
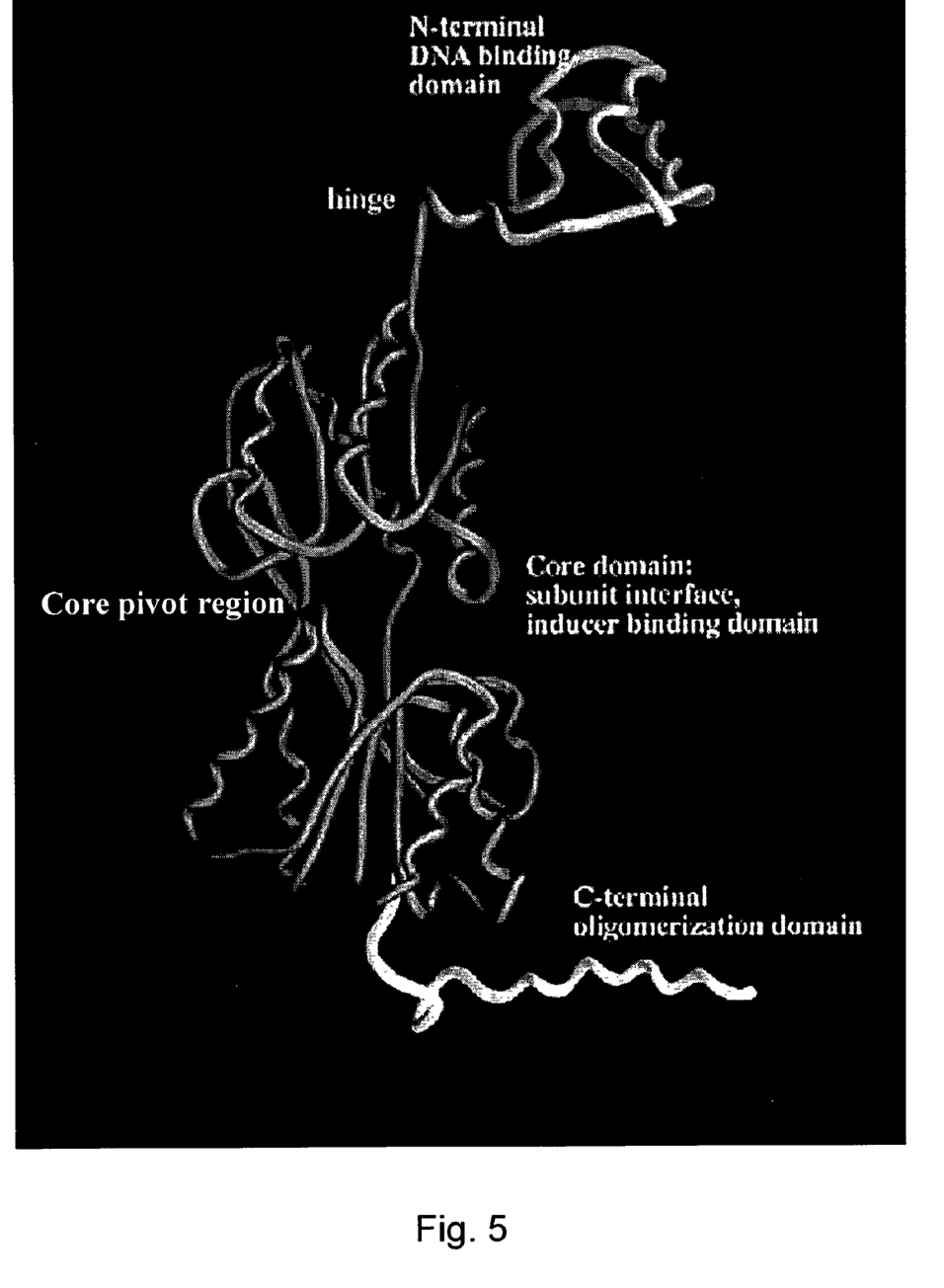
FIG. 5 is a monomer subunit of the lac repressor depicted from its x-ray crystallographic structure and labeled to show defined regions of protein structure and function.

FIG. 2 shows a schematic of the lac repressor protein monomer, and FIG. 3 shows a simplified schematic of the tetramer structure generated by "opening" the tetramer to display the dimer-dimer configuration. FIG. 4 shows a schematic of the fully folded configuration of the tetramer, while an x-ray crystallographic structure of the tetramer bound to operator is depicted in Lewis et al., 1996. A monomer from the x-ray crystallographic structure is shown and the relevant regions are labeled in FIG. 5. The tetramer structure of the lac repressor protein is a dimer-dimer assembly, the two dimers being aligned with their N-terminal domains on the same face of the molecule connected by a four-helical bundle at the base (Friedman et al., 1995; Lewis et al., 1996). This four-helical bundle is the lac repressor protein dimer-dimer assembly motif and is localized to the C-terminal region from about amino acids 340 to 360 (LHR). Monomers of the lac repressor protein will not bind DNA (Daly & Matthews, 1986; Schmitz et al., 1976); therefore, at least a dimer is required to bind DNA.

Homology has been noted between monomeric periplasmic sugar binding proteins in *E. coli* and the core domains of repressor proteins (Mueller-Hill, 1983; Sams et al., 1984; Nichols et al., 1993). SEQ ID NO:1 gives the amino acid sequence of lac repressor protein (Beyreuther et al., 1975; Farabaugh, 1978), while SEQ ID NO:4 gives the amino acid sequence of arabinose binding protein (ABP) (Hogg & Hermodson, 1977). The crystallographic structures of the periplasmic sugar binding proteins, such as ABP, and the lac repressor protein indicate significant structural homology in their sugar binding sites (Lewis et al., 1996; Friedman et al., 1995; Nichols et al., 1993). These structures show that the ligand binding regions consist of two subdomains that surround a binding site. Multiple residues throughout the protein sequences participate in ligand contacts within this site. The two subdomains are connected by multiple linker segments (amino acids 159-165, 289-295, and 316-323) that combine with other residues (amino acids 150-153 and 190-193) to form the "core pivot region." Note that the periplasmic binding proteins are monomeric, while the homologous core domains of the repressor proteins form dimers, a requisite step for successful repressor function.

The present invention relates to altered lac repressor proteins. In certain embodiments of the invention, these altered lac repressor proteins recognize and can bind to lactose operator DNA sequence but have increased affinity for this operator DNA sequence and/or enhanced responsivity to inducer binding. Increased DNA binding provides that the altered repressor protein will bind to lac operator with higher affinity than the wild-type or natural, unmodified lac repressor protein (reducing the "leakiness" of the operator, thereby providing lower constitutive expression from the operator). Furthermore, enhanced inducer responsivity provides that allolactose, IPTG, or other inducing ligand will, at concentrations lower than those required by the natural lac repressor protein, induce the altered lac repressor protein to undergo a conformational change such that affinity for the lac operator is diminished, and transcription from the adjacent promoter by RNA polymerase can take place.

Certain embodiments of the invention provide for lac repressor proteins having wild-type or nearly wild-type affinity (within 10-fold) for LacO DNA sequences, but which are more sensitive to IPTG or are sensitive to other inducing ligands resulting in a more easily inducible inhibitor.

The following definitions are provided in order to aid those skilled in the art to understand the detailed description of the present invention.

"ABP" refers to arabinose binding protein.

"Allolactose" refers to β-1,6-Allolactose, the natural inducer of LacI.

"HTH" refers to the helix-turn-helix domain of lac repressor protein.

"IPTG" refers to isopropyl-β,D-thiogalactoside.

"MUG" refers to methyl umbelliferyl-β,D-galactoside.

"LHR" refers to the leucine heptad repeat domain of lac repressor protein.

"X-gal" refers to 5-bromo-4-chloro-3-indolyl-β,D-galactoside.

The phrase "screening" refers to any method used to identify properties of a specific repressor protein, including but not limited to phenotypic evaluation or biophysical characterization.

The phrase "alternate inducer ligand" means a sugar or another small molecule other than allolactose or IPTG.

The phrase "altered lac repressor protein" means a lac repressor protein which has enhanced responsivity to inducer ligand(s) (that is, enhanced sensitivity to normal inducing sugars, such as IPTG or allolactose, or responsiveness to alternative ligands, such as arabinose, ribose, D-glucose, D-galactose, etc.) and/or recognizes and binds to the LacO$^1$ operator sequence with greater affinity than the natural, unmodified lac repressor protein.

The term "affinity", as used in conjunction with the lac operator or an inducer ligand, is defined as $1/K_d$, where $K_d$ is the concentration of DNA or ligand required to occupy 50% of the available binding sites.

The phrase "natural lac repressor protein" or "wild-type lac repressor protein" means the naturally occurring *E. coli* lac repressor protein (LacI) which recognizes and can bind to the LacO$^1$ operator sequence, and which has a responsivity to allolactose or IPTG.

The phrase a "enhanced inducer responsivity" refers to a LacI protein which is more sensitive ($\geq$2-fold) to IPTG than wild-type LacI or which is responsive to other inducers (i.e., more easily inducible).

The phrase "DNA binding domain of the natural lac repressor protein" refers to the portion of the natural lac repressor protein responsible for mediating the binding of the lac repressor protein to the lac operator DNA sequence and corresponds to approximately amino acids 1-60 of the SEQ ID NO:1.

The phrase "inducer binding domain" refers to amino acids 61-360 of SEQ ID NO:1, or residues 1-306 of SEQ ID NO:4, or residues 1-296 of SEQ ID NO:5, or residues 1-332 of SEQ ID NO:6.

SEQ ID NO:1 gives the amino acid sequence of natural, unmodified lac repressor protein (Beyreuther et al., 1975; Farabaugh, 1978). One embodiment of the present invention relates to an altered lac repressor protein with an amino acid substitution of glycine for the glutamine which occurs at amino acid number 60 in the natural lac repressor protein. This substitution is referred to in shorthand as Gln60Gly. SEQ ID NO:2 gives the amino acid sequence of this mutated, Gln60Gly, protein; SEQ ID NO:3 gives the DNA sequence of a gene capable of coding for this mutant protein. SEQ ID NO:4 gives the amino acid sequence of arabinose binding protein (ABP) (Hogg & Hermodson, 1977). SEQ ID NO:5 gives the amino acid sequence of ribose binding protein. SEQ ID NO:6 gives the amino acid sequence of galactose/glucose binding protein. One skilled in the art will recognize that due to the degenerate nature of the genetic code, multiple DNA sequences are capable of coding for these proteins. These alternative sequences are considered to be within the scope of the present invention.

In addition to the Gln60Gly mutation, other useful mutations provided by the instant invention are listed in Table 1.

TABLE 1

Mutations useful in the Present invention

| Mutation | Characteristics (known or expected) |
| --- | --- |
| Val52Cys | Increased DNA affinity |
| Gln60Gly | Increased DNA affinity |
| Leu148Phe | Enhanced inducer response |
| Leu148Tyr | Enhanced inducer response |
| Ser151Pro | Increased DNA affinity |
| Pro188Ser | Increased DNA affinity |
| Leu296Met | Increased DNA affinity |
| Leu296Ile | Increased DNA affinity |
| Pro320Ala | Increased DNA affinity |
| Pro320Gly | Increased DNA affinity |
| Val321Ile | Increased DNA affinity |
| Val321Leu | Increased DNA affinity |
| Val321Met | Increased DNA affinity |
| Gln60Gly in combination with Leu148Phe | Increased DNA affinity, enhanced inducer response |
| Gln60Gly in combination with Leu148Tyr | Increased DNA affinity, enhanced inducer response |
| Gln60Gly in combination with Ser151Pro | Increased DNA affinity, enhanced inducer response |
| Gln60Gly in combination with Pro188Ser | Increased DNA affinity, enhanced inducer response |
| Gln60Gly in combination with Leu296Met | Increased DNA affinity, enhanced inducer response |
| Gln60Gly in combination with Leu296Ile | Increased DNA affinity, enhanced inducer response |
| Gln60Gly in combination with Pro320A | Increased DNA affinity, enhanced inducer response |
| Gln60Gly in combination with Pro320Gly | Increased DNA affinity, enhanced inducer response |
| Gln60Gly in combination with Val321Ile | Increased DNA affinity, enhanced inducer response |
| Gln60Gly in combination with Val321Leu | Increased DNA affinity, enhanced inducer response |
| Gln60Gly in combination with Val321Met | Increased DNA affinity, enhanced inducer response |
| Gln60Gly in combination with Leu148Phe and Asp274Asn | Increased DNA affinity, induction by D-arabinose |
| Leu148Phe in combination with Asp274Asn | Induction by D-arabinose |

Other mutations useful for this invention can be identified by site-specific or random mutation, primarily targeted to the hinge domain (also known as the hinge region) of the lac repressor protein (this region corresponds to approximately amino acid positions 50-60 in SEQ ID NO:1). In addition, other mutations clustered near the "core pivot region" (defined above) may be identified by site-specific or random mutation that will elicit the characteristics described. Thus, in various alternative embodiments, the present invention provides for lac repressor proteins which:
(i) have increased affinity for the lactose operator DNA;
(ii) have enhanced inducer responsivity (e.g., increased affinity for the natural lac inducers or an affinity for an alternative inducer);
(iii) have an increased affinity for the lactose operator DNA and enhanced inducer responsivity.

In a particular embodiment, a single amino acid change in the lac repressor protein generates the desired increase in its binding affinity for the LacO DNA sequence or enhanced responsivity to inducer. In other embodiments, two or more individual mutations may be combined to provide an altered lac repressor with the desired characteristics. Mutations specifically contemplated as part of the present invention include, but are not limited to the following mutations: Val52Cys, Gln60Gly, Leu148Phe, Leu148Tyr, Ser151Pro, Pro188Ser, Leu296Ile, Leu296Met, Pro320Ala, Pro320Gly, Val321Ile, Val321Leu, and Val321Met. Additionally, it is contemplated that the specific amino acids listed, that is Val52, Gln60, Leu148, etc. could also be mutated to amino acid with properties similar to the listed mutants. For example, it is contemplated that, as an alternative to being mutated to phenylalanine, Leu148 could also be mutated to tyrosine.

TABLE 2

Amino Acids Grouped by Potential Similarity of Function

| Group Similarity Type | Amino Acids |
| --- | --- |
| Related by Size, Aliphatic nature | Alanine, Valine, Leucine, Isoleucine Methionine, Tryptophan |
| Related by Size, Hydroxyl Groups | Serine, Threonine, Alanine, Cysteine |
| Related by Size, Acidity and/or Amide Residues | Aspartate, Glutamate, Asparagine, Glutamine |
| Related by Size, Alkalinity | Lysine, Arginine, Histidine, Leucine, Isoleucine |
| Related by Size, Aromatic nature | Phenylalanine, Tyrosine, Tryptophan, Histidine |
| Related by Size (Small R Groups) | Glycine, Alanine |
| Related by S-Content | Methionine, Cysteine |

In addition to the specific mutations listed, the present invention also provides for other mutations including (a) insertions of one or more amino acids; or (b) deletions of one or more amino acids; and/or (c) other mutation of one or more amino acids; or (d) any combination of "a", "b", and "c". In various embodiments these mutations are carried out to provide altered lac repressors which are mutated at the positions corresponding to the following amino acids of the natural lac repressor (SEQ ID NO:1): Arg51, Val52, Ala53, Lys59, Gln60, Ser61, Phe147, Leu148, Asp149, Val150, Asp152, Gly187, Pro188, Leu189, Leu295, Leu296, Gly297, Leu319, Pro320, Val321, and Ser322.

Another embodiment of the present invention provides for altered lac repressor protein which comprises one or a combination of two or more of the following specific mutations: Val52Cys, Gln60Gly, Leu148Phe, Leu148Tyr, Ser151Pro, Pro188Ser, Leu296Ile, Leu296Met, Pro320Ala, Pro320Gly, Val321Ile, Val321Leu, and Val321Met.

Yet other embodiments of the present invention provide for altered lac repressor proteins comprising the Gln60Gly mutation in combination with one or more of the following mutations: Leu148Phe, Leu148Tyr, Ser151Pro, Pro188Ser, Leu296Ile, Leu296Met, Pro320Ala, Pro320Gly, Val321Ile, Val321Leu, and Val321Met.

One particular embodiment of the invention provides for an altered lac repressor protein comprising the Gln60Gly and Leu148Phe mutations and further comprising an Asp274Asn mutation.

Yet another embodiment of the invention provides for an altered lac repressor protein comprising the Leu148Phe mutation and further comprising a Asp274Asn mutation.

Another particular embodiment of the invention provides for an altered lac repressor protein DNA binding domain which is coupled to a ligand binding domain which is responsive to arabinose.

Altered lac repressor proteins of the present invention can further comprise a tetramerizing domain of a natural lac repressor protein (corresponding to amino acid residues ~340 to 360).

The altered lac repressor proteins of the present invention, which have increased affinity for LacO DNA, can be produced by site-specific mutation of the gene which encodes the lac repressor protein, so as to produce the amino acid substitution of glycine for the glutamine at amino acid number 60 (i.e., Gln60Gly). Similarly, according to an alternative embodiment, the altered lac repressor proteins of the present invention can be produced via other amino acid changes to provide the mutants detailed in Table 1. Such mutations (e.g., Leu148Phe) enhance the repressor's responsivity to IPTG (or other inducing ligands) while maintaining or enhancing their affinity for lac operator DNA sequences when compared to the response of the natural lac repressor protein.

As described above, repressor proteins of the present invention can bind the lac operator with an increased affinity and/or possess an enhanced ligand responsivity. This enhanced ligand responsivity provides that a sugar or other small molecule other than allolactose or IPTG will, at concentrations less ($\geqq$2-fold) than for wild-type lac repressor, induce the altered lac repressor protein to undergo a conformational change such that its affinity for the lac operator DNA sequence is temporarily diminished, and transcription from an adjacent promoter by an RNA polymerase can proceed. Alternatively, the enhanced ligand responsivity may be the result of response to lower concentrations of IPTG.

Sugars useful as alternative inducing ligands in the present invention are generally mono- and di-saccharides, such as arabinose, ribose, glucose, galactose and maltose. Preferred sugars are arabinose, ribose, D-glucose and D-galactose. Arabinose is a particularly preferred sugar. SEQ ID NO:4 gives the amino acid sequence of arabinose binding protein (ABP) (Hogg & Hermodson, 1977). Other small molecules useful in the present invention include amino acids, such as glutamine, leucine and ornithine; purines; pyrimidines; and small organic ions, among others.

Altered lac repressor proteins can be made by site-specific mutagenesis, as was done to create Gln60Gly, or by random mutagenesis and screening for proteins with increased affinity for $O^1$ operator sequence and normal induction behavior. Recombinant DNA techniques are well known to those of skill in the art, and can be found, for example, in *DNA Cloning: A Practical Approach*. Glover and Hames, Eds. (1995) or *Molecular Cloning: A Laboratory Manual* (1989). Using PCR-based methods, chemical mutagenesis, or mutator strains to introduce nucleotide changes in vivo (e.g., Stratagene (La Jolla, Calif.), *Epicurian coli*, XL1-Red), the plasmid containing the lac repressor protein gene is subjected to sequential rounds of mutagenesis and screening. After, mutagenesis, the screening procedure delineated below is followed to test for an active repressor protein. Finally, the DNA from each of the positive colonies is sequenced. Alternate screens known to those skilled in the art (e.g., using a toxic gene) can also be used which will result in the identification of active repressor proteins.

The homology between monomeric periplasmic sugar binding proteins and the inducer binding region of the core domain of the lac repressor protein allows repressor proteins of the present invention can be produced by (a) site-specific (including the mutations set out in Table 1) and/or random mutagenesis of the inducer binding region of the core domain of natural lac repressor protein, and (b) screening for proteins with normal affinity for $O^1$ operator sequence and enhanced responsivity to IPTG or other ligand, as was done for Leu148Phe. Recombinant DNA techniques are well known to those of skill in the art (see previous paragraph for specific references). Using PCR-based methods, chemical mutagenesis, or mutator strains to introduce nucleotide changes in vivo (e.g., Stratagene (La Jolla, Calif.), *Epicurian coli*, XL1-Red), the plasmid containing the lac repressor protein gene is subjected to sequential rounds of mutagenesis and screening.

After mutagenesis, the screening procedure delineated below is followed to test for an active repressor protein with enhanced ligand responsivity. Finally, the DNA from each of the positive colonies is sequenced. Alternate screens known to those skilled in the art can also be used which will result in the identification of active repressor proteins.

Correspondingly, altered lac repressor proteins can also be made by combining the DNA-binding domain (HTH) of altered lac repressor protein, which corresponds to about amino acids 1-60 of SEQ ID NO:2, and, optionally, the tetramerization domain (LHR) elements of natural lac repressor protein (corresponding to about amino acids 340 to 360 of SEQ ID NO:1) with a ligand binding protein, such as ABP (SEQ ID NO:4). Combination of these domains is accomplished by fusing the DNA encoding the HTH domain and the hinge domain of the lac repressor protein to the N-terminus of the alternative ligand binding protein DNA, ABP for example, with spacing chosen after visual inspection of aligned LacI and ABP structures. Again, the necessary recombinant DNA techniques are well known to those skilled in the art. The DNA encoding the LHR domain from lac repressor protein is then added to sites carefully selected by visual inspection of the structure at the C-terminus of the ligand binding protein DNA. The LHR element can be deleted for the construction of a dimeric repressor protein with enhanced responsivity to ligand. However, in order to significantly bind the lactose operator, the repressor protein must form at least a dimer. In order to be induced, the repressor protein must be able to transmit an allosteric message from the inducer binding site to the DNA binding site. When monomeric ligand binding proteins are fused to the DNA-binding domain of the lac repressor protein, the resulting construct is a monomer. This monomeric construct can be subjected to multiple rounds of random mutagenesis in order to introduce the amino acid changes necessary for the new construct to form a dimer and transmit the allosteric message between binding sites. The resulting mutants are then selected for ability to bind lactose operator.

In other embodiments of the present invention, the ligand binding proteins useful in the present invention include any protein which binds a sugar or other small molecule other than allolactose or IPTG and which has substantial sequence and/or structural homology with the core domain, or ligand binding site, of natural lac repressor protein. Examples of ligand binding proteins useful in the present invention are ABP (SEQ ID NO:4), ribose binding protein (RBP) (SEQ ID NO:5), and D-glucose/D-galactose binding protein (GBP) (SEQ ID NO:6). Amino acid sequences for these binding proteins and their alignment with the lac repressor protein core domain can be found in the literature (Nichols et al., 1993). Similar ligand binding proteins with structural homology can be found by examining the family of periplasmic binding proteins from *E. coli*. Exemplary ligand binding proteins can be found in: Hsiao et al. (1996), glutamine-binding protein; Olah et al. (1993), leucine/isoleucine/valine-binding protein; Oh et al. (1994), lysine/arginine/ornithine-binding protein; Spurlino et al. (1991), maltose/maltodextrin-binding protein; Pflugrath & Quiocho (1988), sulfate-binding protein; Tam & Saier (1993), solute-binding receptors; and Matsuo & Nishikawa (1994), spermidine/putrescine-binding protein. Preferably, the ligand binding protein is ABP due to the ready availability and low cost of arabinose for use as an inducer.

To test an altered lac repressor protein, the coding sequence for the altered lac repressor protein can be cloned into an expression vector. The expression vector can then be placed into bacterial or eukaryotic cells containing a reporter gene under lac operator control to test for an active repressor protein. For example, a reporter containing *E. coli* β-galactosidase (encoded by lacZ) has been constructed by excising the lacZ gene under control of the lac operator from the plasmid pCR2.1 (Invitrogen) and inserting it into plasmid pACYC184 (New England Biolabs). This new composite reporter plasmid is named pZCam and can be co-transformed or electroporated into bacteria with the plasmids containing the coding sequences of altered lac repressor proteins. Host cells for these plasmids should have neither lactose repressor nor β-galactosidase proteins (i.e., the cells are lacI⁻ lacZ⁻). Next, these bacteria are plated in the presence of either methyl umbelliferyl-β-D-galactoside (MUG) or 5-bromo-4-chloro-3-indolyl-β,D-galactoside (X-gal) as indicators to determine whether an active repressor protein is present (white colonies). In the presence of an inducer sugar, colonies containing inducer-responsive repressor protein will be fluorescent (MUG) or blue (X-gal). Alternatively, the coding sequence can be cloned into any expression vector known in the art and transformed into *E. coli* that are lacI⁻, preferably ΔlacI, and lacpOz⁺. The lacpOz region can be on a different, but compatible, plasmid or in the bacterial genome. Colonies containing active repressor protein will be white in the absence of an inducer and fluorescent (MUG) or blue (X-gal) in the presence of an inducer. Specific amino acid changes that result in increased operator binding affinity or enhanced ligand responsivity can be determined. LacI derivatives with appropriate properties are then isolated and characterized in vitro for their (a) $O^1$ operator DNA binding properties in the absence and presence of the appropriate inducer ligand and (b) inducer ligand binding properties in the absence and presence of operator DNA. Purified proteins can be obtained by standard protein purification methods known to those of skill in the art.

Random mutagenesis methods can also be used to enhance operator DNA binding in the lac repressor protein or generate enhanced ligand responsivity. In this method, random mutagenesis of the DNA encoding lac repressor protein is followed by screens for increased operator binding and sensitivity to inducer ligand in the protein products. Both site-specific and random mutagenesis methods are well known in the art and can be used in the practice of the present invention.

Mutants can be screened by phenotypic analysis as described above. In the preferred forms, the plasmid containing the gene for altered lac repressor protein is either co-transformed with the reporter plasmid pZCam or is transformed into *E. coli* that are ΔlacI and lacpOz⁺. Introduction of wild-type lac repressor protein into bacteria containing pZCam or into the ΔlacI/lacpOz⁺ bacteria results in white colonies in the presence of MUG or X-gal. In contrast, in the presence of IPTG or the alternative ligand, the colonies are fluorescent (MUG) or blue (X-gal). Natural lac repressor protein subjected to mutation can be screened for: 1) increased operator affinity by determining the background level of lacZ expression by colony color; and 2) sensitivity to ligand by using varied concentrations of IPTG (or the alternative ligand). Colonies that are white without ligand and at least slightly blue (X-gal) or fluorescent (MUG) in the presence of IPTG (or the alternative ligand) under conditions where wild-type colonies are white/non-fluorescent indicate that the modified repressor possesses enhanced responsivity to inducer ligand.

The altered lac repressor proteins of the present invention can be used in any manner natural lac repressor protein is used. Such uses include regulating expression of genes in bacterial cells and controlling expression and facilitating transcription in eukaryotic systems. The altered lac repressor protein can be encoded on a plasmid and incorporated into a bacterial or eukaryotic cell. For example, altered lac repressor proteins can be used to control the expression of T7 polymerase, a protein that is unique to a specific phage that infects *Escherichia coli*. A wide variety of proteins are expressed under control of the T7 polymerase promoter, e.g., p53 tumor suppressor protein, in cells where the T7 polymerase in turn is under lac repressor protein control.

By using altered lac repressor proteins which exhibit increased affinity for $LacO^1$ DNA sequence, the enhanced repression derived from the increased $O^1$ affinity diminishes the "leakiness" (i.e., the amount of constitutive transcription of the gene in the absence of inducing sugars) of the system thereby precluding expression of the target protein until the inducer ligand is added.

The following examples are included to demonstrate preferred embodiments of the invention. Those of skill in the art will appreciate that the techniques disclosed in the examples that follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

The mutation Gln60Gly was introduced in the natural LacI protein by site-directed mutagenesis. The product protein exhibits increased affinity for $O^1$ operator sequences ($K^d=4\times 10^{-12}$ M for Gln60Gly versus $K_d=1.2\times10^{-11}$ M for wild-type LacI). The protein exhibits wild-type affinity ($K_d>10^{-7}$ M) for $O^1$ operator sequences in the presence of 1 mM IPTG, and appears to have close to normal responsivity to inducer (Falcon and Matthews, 1999). This protein can enhance repression and can be utilized to control expression of genes that may be toxic or deleterious to the cell in a number of applications.

EXAMPLE 2

The hinge region of the wild-type LacI sequence can be examined for sites that, based on structural analysis (Lewis et al., 1996), would enhance DNA binding without disruption of induction response. These amino acid changes can be introduced by site-directed mutagenesis to alter selected amino acids in the hinge region and the products examined by screening and by isolation and characterization. For example, the mutation of lac repressor amino acid 52 from Val to Cys (Val52Cys) results in production of a protein with increased affinity for the lac operator DNA and normal response to inducer in reduced form. However the Val52Cys mutant is physiologically unstable and difficult to purify (Falcon et al., 1997). Conversely, Gln55Glu and Gly58+1 (which inserts a Gly between positions 58 and 59) mutants of the lac repressor result in a decreased affinity for lac operator DNA (Falcon, Catherine M., Ph.D. Thesis, Rice University, 1999).

EXAMPLE 3

The gene encoding the natural lac repressor protein can be subjected to random mutagenesis, using XL-1 Red bacterial cells (Stratagene, La Jolla, Calif.), chemical mutagenesis, or polymerase chain reaction methods, to alter the operator binding affinity. Mutants of the lac repressor protein can then be screened in the fluorescent/non-fluorescent (MUG) or blue/white (X-gal) assay as described above to detect binding to operator DNA and responsivity to inducer ligands. Products identified with appropriate properties (such as increased affinity for LacO DNA sequences) can be sequenced and the protein products isolated and characterized in vitro. For example, Pro320Ala was identified by random mutagenesis and phenotypic screening for enhanced inducer responsivity (see example 11). Biochemical analysis demonstrates increased DNA affinity with normal inducer responsivity.

EXAMPLE 4

The gene encoding the natural lac repressor protein can be subjected to random mutagenesis by polymerase chain reaction to alter its properties. Mutants can then be screened for enhanced responsivity to IPTG. The Leu148Phe mutant protein was identified in this manner. Biochemical analysis demonstrates slightly diminished DNA affinity and enhanced responsivity to IPTG.

EXAMPLE 5

The gene encoding the natural lac repressor protein can be subjected to random mutagenesis by polymerase chain reaction to alter its properties. Mutants can then be screened for enhanced responsivity to IPTG or response to an alternate ligand. The "core pivot region" can be targeted for effects similar to those observed for Leu148Phe.

EXAMPLE 6

The mutation Gln60Gly that generates increased affinity for operator sequences can be combined with Leu148Phe that generates diminished affinity for operator sequences but enhanced responsivity to IPTG. The double mutant Gln60Gly/Leu148Phe exhibits increased affinity for operator sequence compared to Leu148Phe (affinity comparable to wild-type lac repressor) and enhanced inducer responsivity comparable to Leu148Phe. Thus, combinations of mutations may generate repressors with desirable characteristics for control of expression regulated by the lac operator DNA sequence.

EXAMPLE 7

The altered lac repressor proteins with increased operator affinity and normal inducer response produced as in Examples 1-3 can be used to control the expression of any lac repressor protein-regulated expression system, e.g., T7 polymerase in E. coli, as found in multiple commercial vectors, by introducing the plasmid encoding the altered lactose repressor protein on a plasmid compatible with the other constructs present. Enhanced repression by this protein enhances repression of the gene under control until inducing ligand is added.

EXAMPLE 8

The HTH and hinge region of the modified lac repressor protein (comprising approximately amino acids 1-60) as prepared by Examples 1, 2, or 3 (the Gln60Gly mutant for example) can be fused to the N-terminus of ABP (SEQ ID NO:4), and the LHR region of natural lac repressor protein fused to the C-terminus of ABP to produce an altered lac repressor protein which comprises approximately amino acids 1-306 of SEQ ID NO:4. The coding sequence for the chimera can then be cloned into pZCam expression vector. The plasmid can be transformed or electroporated into lacI$^-$ lacZ$^-$ E. coli. Following mutagenesis using PCR-based methods, chemical mutagenesis or mutator strains to produce oligomer formation and to allow allosteric communication, the bacteria can be screened in the phenotypic screen described above to determine active repressor protein with the appropriate DNA affinity and sugar ligand response.

EXAMPLE 9

A lac repressor protein with responsivity to ribose can be prepared by fusing approximately amino acids 25 to 296 of the RBP of SEQ ID NO:5 to the HTH, hinge region, and LHR region of the modified lac repressor as was described for ABP in Example 5.

EXAMPLE 10

A lac repressor protein with responsivity to galactose or glucose can be prepared by fusing approximately amino acids 24 to 332 of the GBP of SEQ ID NO:6 to the HTH, hinge region, and LHR region as was described for ABP in Example 5.

EXAMPLE 11

A lac repressor protein Pro320Ala was identified by random mutagenesis using polymerase chain reaction methods and phenotypic screening. This protein binds to operator DNA with 10-fold higher affinity than wild-type lac repressor and yet still exhibits wild-type inducer responsivity.

EXAMPLE 12

The HTH and hinge region of modified lac repressor protein (e.g., Gln60Gly) can be fused to the N-terminus of ABP, without the LHR region at the C-terminus. The resulting monomeric construct can be subjected to multiple rounds of random mutagenesis using PCR-based methods, chemical mutagenesis or mutator strains. The coding sequence for the mutated chimera can then be cloned into an expression vector and co-transformed with pZCam. The plasmid can be transformed or electroporated into lacI$^-$ lacZ$^-$ E. coli. The bacteria can be screened in the blue/white (X-GAL) or fluorescent/nonfluorescent (MUG) screen described above to determine active repressor protein. The DNA from each of the positive colonies can then be sequenced.

EXAMPLE 13

Natural lac repressor protein and ABP amino acid sequences can be compared to determine amino acid changes to be made. Modified lac repressor protein (e.g., Gln60Gly) can then be subjected to site-directed mutagenesis or other methods to alter selected amino acids in the inducer binding region. Mutants of the lac repressor protein can be screened in the blue/white (X-GAL) or fluorescent/nonfluorescent (MUG) assay as described above to detect responsivity to arabinose.

EXAMPLE 14

The altered lac repressor proteins with responsivity to an alternate inducer such as arabinose, ribose, glucose, or galactose produced as in Examples 4-11 can be used to control the expression of lac repressor protein-regulated promoter-operator sequences, including T7 polymerase in E. coli, as found in multiple commercial vectors, by introducing the plasmid encoding the altered lactose repressor protein on a plasmid compatible with the other constructs present. For example, an altered lac repressor responsive to arabinose can be created by fusing a DNA sequence encoding the ligand binding domain of an arabinose binding protein (e.g., amino acids 1-306 of SEQ ID NO:4) to the DNA binding domain of the natural or an altered lac repressor. The presence of alternate inducer sugar results in decreased affinity for the lac operator and consequent production of mRNA for any gene under control of the promoter-operator sequence.

All of the compositions and methods disclosed and claimed herein can be made and executed without undue experimentation in light of the present disclosure. While the compositions and methods of this invention have been described in terms of preferred embodiments, it will be apparent to those of skill in the art that variations can be applied to the compositions and methods and in the steps or in the sequence of steps of the methods described herein without departing from the concept, spirit and scope of the invention. More specifically, it will be apparent that certain agents which are both chemically and physiologically related can be substituted for the agents described herein while the same or similar results would be achieved. All such similar substitutions and modifications apparent to those skilled in the art are deemed to be within the spirit, scope and concept of the invention as defined by the appended claims.

REFERENCES

The following references (and references contained therein), to the extent that they provide exemplary procedural or other details supplementary to those set forth herein, are specifically incorporated herein by reference.

Beyreuther, K.; Adler, K.; Fanning, E.; Murray, C.; Klemm, A.; Geisler, N. *Eur. J. Biochem.* 59: 491-509 (1975).
Brennan, R. G.; Matthews, B. W. *J. Biol. Chem.* 264: 1903-1906 (1989).
Butler, A. P.; Revzin, A.; von Hippel, P. H. *Biochemistry* 16: 4757-4768 (1977).
Daly, T. J.; Matthews, K. S. *Biochemistry* 25: 5474-5478 (1986).
Falcon, C. M. Ph.D. Thesis, Rice University, April 1999.
Falcon, C. M. and Matthews, K. S. *J. Biol. Chem.* 274: 30849-30857 (1999).
Falcon, C. M.; Swint-Kruse, L.; Matthews, K. S. *J. Biol. Chem.* 272: 26818-26821 (1997).
Farabaugh, P. J. *Nature* 274: 765-769 (1978).
Friedman, A. M.; Fischmann, T. O.; Steitz, T. A. *Science* 268: 1721-1727 (1995).
Gilbert, W.; Mueller-Hill, B. *Proc. Natl. Acad. Sci. U.S.A.* 56: 1891-1898 (1966).
Glover, D. M.; Hames, B. D. eds. *DNA Cloning. A Practical Approach* 2nd edition. IRL Press, New York (1995).
Hogg, R. W.; Hermodson, M. A. *J. Biol. Chem.* 252: 5135-5141 (1977).
Hsiao, C. D.; Sun, Y. J.; Rose, J.; Wang, B. C. *J. Mol. Biol.* 262: 225-242 (1996).
Jacob, F.; Monod, J. *J. Mol. Biol.* 3: 318-356 (1961).
Jobe, A.; Bourgeois, S. *J. Mol. Biol.* 69: 397-403 (1972).
Kalodimos, C. G.; Folkers, G. E.; Boelens, R.; Kaptein, R. *Proc. Natl. Acad. Sci. U. S. A.* 98:6039-6044 (2001).
Lewis, M.; Chang, G.; Horton, N. C.; Kercher, M. A.; Pace, H. C.; Schumacher, M. A.; Brennan, R. G.; Lu, P. *Science* 271: 1247-1254 (1996).
Lin, S.-Y.; Riggs, A. D. *Cell.* 4: 107-111 (1975).
Matthews, K. S.; Nichols, J. C., *Prog. Nucl. Acid Res. Mol. Biol.* 58: 127-164 (1998).
Matsuo, Y.; Nishikawa, K. *FEBS Lett.* 345: 23-26 (1994).
Miller, J. H.; Reznikoff, W. S. eds. *The Operon.* Cold Spring Harbor Laboratory Press, Cold Spring Harbor, N.Y. (1980).
Mueller-Hill, B. *Nature* 302: 163-164 (1983).
Nichols, J. C.; Vyas, N. K.; Quiocho, F. A.; Matthews, K. S. *J. Biol. Chem.* 268: 17602-17612 (1993).
Ogata and Gilbert; *Proc. Natl. Acad. Sci. U.S.A.* 56: 1891-1898 (1978)
Oh, B. H.; Ames, G. F.; Kim, S. H. *J. Biol. Chem.* 269: 26323-26330 (1994).
Olah, G. A.; Trakhanov, S.; Trewhella, J.; Quiocho, F. A. *J. Biol. Chem.* 268: 16241-16247 (1993).
Pflugrath, J. W.; Quiocho, F. A. *J. Mol. Biol.* 200: 163-180 (1988).
Riggs, A. D.; Bourgeois, S. *J. Mol. Biol.* 34: 361-364 (1968).
Sambrook et al. *Molecular Cloning: A Laboratory Manual* 2nd edition. Cold Spring Harbor Laboratory Press, Cold Spring Harbor, N.Y. (1989).
Sams, C. F.; Vyas, N. K.; Quiocho, F. A.; Matthews, K. S. *Nature* 310: 429-430 (1984).
Schmitz, A.; Schmeissner, U.; Miller, J. H.; Lu, P. *J. Biol. Chem.* 251: 3359-3366 (1976).
Spurlino, J. C.; Lu, G. Y.; Quiocho, F. A. *J. Biol. Chem.* 266: 5202-5219 (1991).
Tam, R.; Saier, Jr., M. H. *Microbiol. Rev.* 57: 320-346 (1993).
Weickert, M. J.; Adhya, S. *J. Biol. Chem.* 267: 15869-15874 (1992).
Whitson, P. A.; Matthews, K. S. *Biochemistry* 25: 3845-3852 (1986).

What is claimed is:

1. An altered lac repressor protein, that:
   a) has an enhanced inducer responsivity relative to a wild-type lac repressor protein, wherein the altered lac repressor protein comprises the following amino acid changes relative to the wild-type lac repressor protein: Leu148Phe in combination with Asp274Asn; or
   b) has both an increased binding affinity for LacO DNA sequence and an enhanced inducer responsivity relative to a wild-type lac repressor protein, wherein the altered lac repressor protein comprises a combination of two or more amino acid changes, relative to the wild-type lac repressor protein, wherein the amino acid changes are selected from the group consisting of:
   Gln60Gly in combination with Leu148Phe,
   Gln60Gly in combination with Leu148Tyr,
   Gln60Gly in combination with Pro188Ser,
   Gln60Gly in combination with Leu296Met,
   Gln60Gly in combination with Leu296Ile,
   Gln60Gly in combination with Pro320Ala,
   Gln60Gly in combination with Pro320Gly,
   Gln60Gly in combination with Val321Ile,
   Gln60Gly in combination with Val321Leu,
   Gln60Gly in combination with Val321Met, and
   Gln60Gly in combination with Leu148Phe and Asp274Asn.

2. The altered lac repressor protein of claim 1 that comprises the Gln60Gly mutation, the Leu148Phe mutation and the Asp274Asn mutation.

3. The altered lac repressor protein of claim 1 that comprises the Gln60Gly and Leu148Phe mutation.

4. The altered lac repressor protein of claim 1 that comprises the Leu148Phe mutation in combination with the Asp274Asn mutation.

5. The altered lac repressor protein of claim 1 that binds LacO DNA with increased affinity relative to wild-type lac repressor protein.

6. The altered lac repressor protein of claim 1 that responds to inducer ligand at lower concentrations of inducer ligand than does the wild-type lac repressor protein.

7. A bacterium or eukaryotic cell, comprising DNA encoding the repressor protein of claim 1.

8. The bacterium of claim 7 which is *Eseherichia coli*.

* * * * *

UNITED STATES PATENT AND TRADEMARK OFFICE
CERTIFICATE OF CORRECTION

PATENT NO.       : 7,390,645 B2                                               Page 1 of 1
APPLICATION NO.  : 10/197053
DATED            : June 24, 2008
INVENTOR(S)      : Foster et al.

It is certified that error appears in the above-identified patent and that said Letters Patent is hereby corrected as shown below:

Claim 8, column 28, line 21, delete "*Eseherichia*" and insert --*Escherichia*--.

Signed and Sealed this

Nineteenth Day of August, 2008

JON W. DUDAS
*Director of the United States Patent and Trademark Office*